US007615382B2

(12) United States Patent
Wang et al.

(10) Patent No.: US 7,615,382 B2
(45) Date of Patent: Nov. 10, 2009

(54) MAGNETIC SIFTER

(75) Inventors: Shan X. Wang, Portola Valley, CA (US); Nader Pourmand, San Mateo, CA (US); Robert L. White, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 449 days.

(21) Appl. No.: 11/595,818

(22) Filed: Nov. 9, 2006

(65) Prior Publication Data

US 2007/0181466 A1 Aug. 9, 2007

Related U.S. Application Data

(60) Provisional application No. 60/735,558, filed on Nov. 9, 2005.

(51) Int. Cl.
*G01N 33/553* (2006.01)
*B03C 1/30* (2006.01)

(52) U.S. Cl. ....................... 436/526; 436/518; 436/538; 209/38; 209/214; 209/215

(58) Field of Classification Search ................. 436/526, 436/518, 538; 209/38, 214, 215
See application file for complete search history.

(56) References Cited

U.S. PATENT DOCUMENTS

| | | | |
|---|---|---|---|
| 5,655,665 | A | 8/1997 | Allen et al. |
| 6,890,426 | B2 | 5/2005 | Terstappen et al. |
| 2004/0009614 | A1 | 1/2004 | Ahn et al. |
| 2005/0100930 | A1 | 5/2005 | Wang et al. |
| 2006/0008823 | A1 | 1/2006 | Kemp et al. |

*Primary Examiner*—Mark L Shibuya
*Assistant Examiner*—Pensee T Do
(74) *Attorney, Agent, or Firm*—Lument Patent Firm

(57) ABSTRACT

The present invention provides a magnetic sifter that is small in scale, enables three-dimensional flow in a direction normal to the substrate, allows relatively higher capture rates and higher flow rates, and provides a relatively easy method of releasing captured biomolecules. The magnetic sifter includes at least one substrate. Each substrate contains a plurality of slits, each of which extends through the substrate. The sifter also includes a plurality of magnets attached to the bottom surface of the substrate. These magnets are located proximal to the openings of the slits. An electromagnetic source controls the magnitude and direction of magnetic field gradient generated by the magnets. Either one device may be used, or multiple devices may be used in series. In addition, the magnetic sifter may be used in connection with a detection chamber.

27 Claims, 12 Drawing Sheets

MAGNETIC SIFTER

CROSS-REFERENCE TO RELATED APPLICATIONS

This application claims priority from U.S. Provisional Patent Application No. 60/735,558, filed Nov. 9, 2005, which is incorporated herein by reference.

STATEMENT REGARDING FEDERALLY SPONSORED RESEARCH OR DEVELOPMENT

This invention was made in part with government support under grant number N00014-02-1-0807 from the Defense Advanced Research Projects Agency (DARPA), United States Navy, and 1U54CA119367-01 from the United States National Cancer Institute. The government has certain rights in this invention.

FIELD OF THE INVENTION

The present invention relates generally to sample preparation. More particularly, the present invention relates to a magnetic sifter. The magnetic sifter is especially suitable for preparation of biological samples.

BACKGROUND

Numerous biomedical applications require rapid and precise identification and quantitation of biomolecules present in relevant biological and environmental samples. The starting point in such experiments is an appropriate sample preparation procedure, which often determines if the experimental outcome is successful or not. For example, sample collection, pre-purification, and preparation procedures are crucial in molecular diagnostics such as genomic and proteomic analyses. These analyses usually depend on specific hybridization or affinity binding between DNA/RNA/protein targets (unknown) and probes (known). The specificity of hybridization or affinity binding can be negatively affected by the presence of abundant impurities. Furthermore, the concentration of target molecules may vary by many orders of magnitude and fall out of the dynamic range of the biosensors used to detect them.

Despite the importance of sample preparation methods, no universal or standard sample preparation protocols exist in the biomedical community. Variations in sample preparation may contribute to major discrepancies in the quantity and type of biomolecules identified by different laboratories, even though the same reagents and biosensors (or biochips) are employed. Therefore, better and more affordable sample preparation methods and tools are still in great demand.

There are a number of devices available for sorting or capturing biomolecules of interest using magnetic sorters. With these devices, a wall of the device contains a magnet, fluid is passed over the magnet in a planar configuration, and magnetic probes attached to a biomolecule of interest sticks to the magnet, allowing impurities to pass through. These devices have a number of shortcomings, including large size, low capture rates, low flow rates, and cumbersome methods of releasing captured biomolecules. Accordingly, there is a need in the art to develop a new magnetic device that is small in scale, enables three dimensional flow normal to the substrate, allows relatively higher flow rates and higher capture rates, and provides a relatively easy method of releasing captured biomolecules.

SUMMARY OF THE INVENTION

The present invention provides a magnetic sifter with all of the above properties. The magnetic sifter includes at least one substrate. Each substrate contains a plurality of slits, each of which extends through the substrate. The sifter also includes a plurality of magnets attached to the bottom surface of the substrate. These magnets are located proximal to the openings of the slits. An electromagnetic source controls the magnitude and direction of magnetic field gradient generated by the magnets. Either one device may be used, or multiple devices may be stacked on top of one another. In addition, the magnetic sifter may be used in connection with a detection chamber.

Preferably, the magnets are made of a soft magnetic material and the substrate is made of silicon, silicon oxide, or silicon nitride. In the latter two cases, the sifter also preferably includes a support layer. The support layer preferably has a plurality of openings, each of which connects to a plurality of slits in the substrate.

The present invention also provides a method of preparing a biological sample with the inventive magnetic sifter. With this method, a biological sample is mixed with capture probes. The capture probes are labeled with magnetic tags, such that at least one target biomolecule binds to the capture probes. A magnetic field is then generated in the magnetic sifter with an electromagnetic source. The biological sample/capture probe mixture is then passed through the magnetized magnetic sifter. In this way, capture probes, bound to the at least one biomolecule, are captured by the magnetic sifter, whereas impurities in the biological sample pass through. At this point, the capture probes may be kept bound to the magnetic sifter. Alternatively, the capture probes may be released by rotating the direction of the applied magnetic field by 90 degrees. This serves to reduce the magnitude of the magnetic field gradient. The magnetic sifter may also be flushed with a washing buffer during this process to aid in the removal of capture probe. The biomolecule of interest may be separated from the capture probe at this point, or prior to release of the capture probe.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
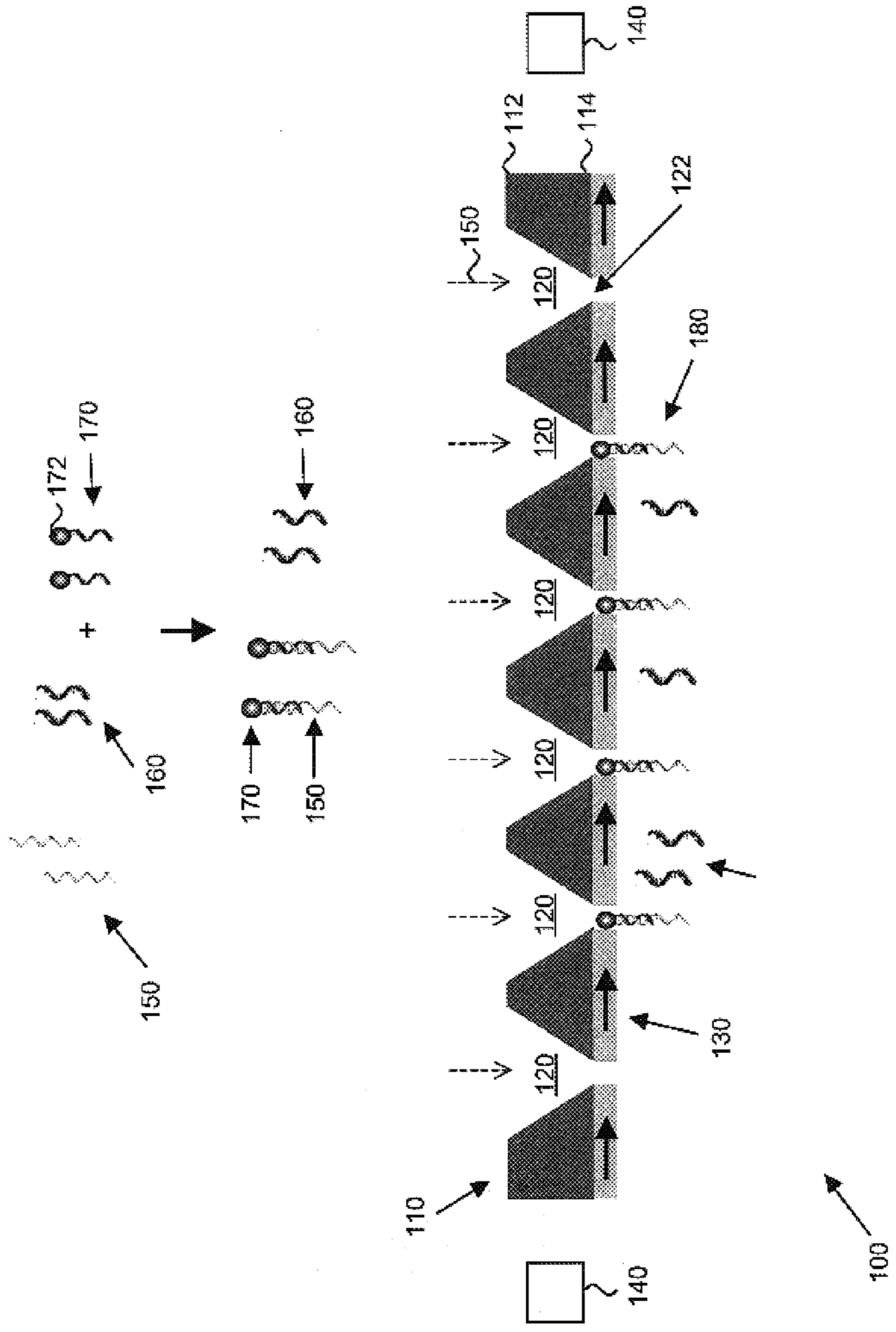
FIG. 1 shows a cross-sectional view of a magnetic sifter according to the present invention.

FIG. 1 shows a magnetic sifter 100 according to the present invention. Magnetic sifter 100 includes a substrate 110, with top surface 112 and bottom surface 114. A plurality of slits 120 extends through substrate 110. These slits are preferably between about 0.5 μm and about 10 μm wide at bottom surface 114. Also preferably, the distance between neighboring slits is between about 0.5 μm and about 10 μm. Substrate 110 includes magnets 130 on its bottom surface 114. Magnets 130 are preferably soft magnets. As shown, magnets 130 are proximal to openings 122 of slits 120. Magnetic sifter 100 also includes an electromagnetic source 140 for controlling the magnitude and direction of a magnetic field gradient generated by magnets 130. Preferably, electromagnetic source 140 induces magnets 130 to generate a magnetic field gradient in the range of about 0.1 T/μm and about 1 T/μm at the openings 122 of the slits 120. Magnetic sifter 100 is preferably micromachined.

Magnetic sifter 100 can be used in the following way. A raw sample containing target molecules 150 and impurities 160 are first mixed with specific capture probes 170 labeled with magnetic tags 172. The magnetic tags 172 may be magnetic beads or any other magnetic tag known in the art. The magnetic tags are preferably magnetic nanotags, as described in U.S. patent application Ser. No. 10/829,505, by Wang et al, which is incorporated by reference herein. The size of slits 120 is scaled accordingly to accommodate the size of the utilized magnetic tags. In the embodiment of the invention shown, a sequence of the capture probes 170 is complementary to a sequence of the target molecules 150 so that they can readily hybridize under appropriate conditions. In this case, the target molecules 150 are nucleic acid, such as RNA or DNA. The impurities 160 are not complementary with the capture probes 170 so that they remain unchanged in the mixture. In another embodiment, the capture probes 170 are antibodies attached to a magnetic nanotag 172, and the target molecule 150 is a protein or peptide. The mixture is then passed through magnetic sifter 100, with the direction of flow indicated by dashed arrows 150. It is also feasible to reverse the flow direction. The magnetic nanotags 172 in capture probes 170, which have zero remanent magnetization in the absence of an applied magnetic field, become magnetized by magnets 130 and trapped at the edges of magnets 130 along with targets 150, while the impurities 160 pass through the slits. (The direction of the magnetic field in this and subsequent figures is indicated by bold arrows).

Figure 2:
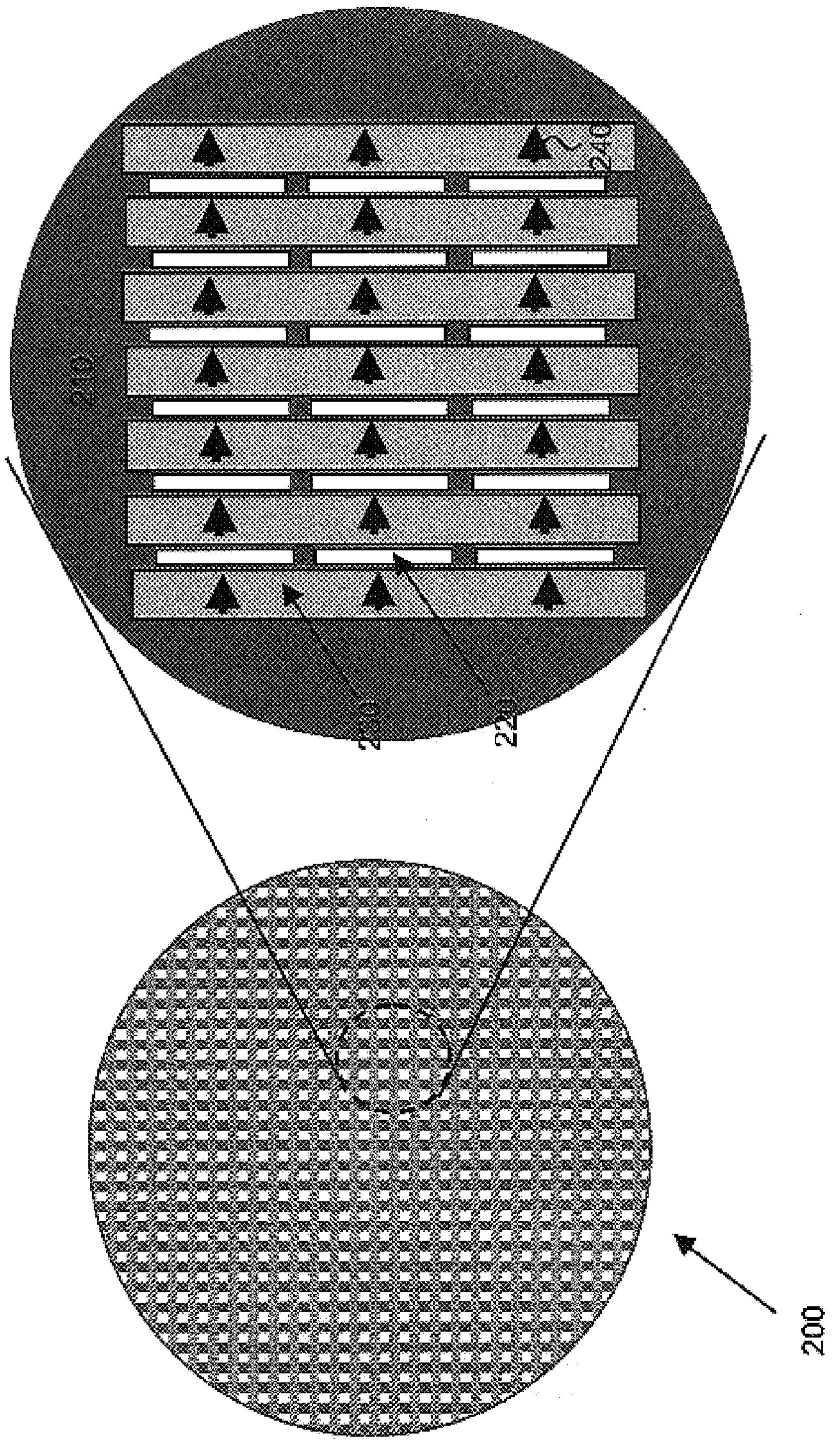
FIG. 2 shows a bottom view of a magnetic sifter according to the present invention.

FIG. 2 shows a bottom view of a magnetic sifter 200. As shown in the blown up section on the right of FIG. 2, in order to achieve a high throughput (or flow rate) of samples, slits 220 are preferably etched into substrate 210 in a rectangular shape so that at least one dimension is not a limiting factor to fluid flow. Furthermore, the rectangular shape is conducive to generating a strong horizontal magnetic field by magnets 230, which ensures capture of most of the magnetic nanotags and thus the target molecules.

Depending on the gap between soft magnets, a horizontal field gradient ranging from ~0.01 T/μm to ~1 T/μm can be readily attained. As an example, consider iron oxide nanotags in aqueous solution. Presume that their radius is r=7 nm, their saturation magnetization is M=340 emu/cc, water viscosity is $\eta=8.9\times10^{-4}$ kg/(m s), and the field gradient near a 0.5 μm wide gap of the soft magnets is ∇B~1 T/μm at a distance of d=0.15 μm from the gap edge. Then, the drift velocity Δv of the nanotags is determined by the balance between the magnetic force and viscous force (Stoke's law):

$$\Delta v = \frac{m\cdot\nabla B}{6\pi\eta r}$$

$$= \frac{340\cdot1000\ (\text{A/m})\cdot(4/3)\cdot(7\cdot10^{-9}\ \text{m})^3\cdot10^6\ (\text{T/m})}{6\cdot(8.9\cdot10^{-4}\ \text{kg/m}\cdot\text{s})\cdot7\cdot10^{-9}\ \text{m}}$$

$$= 4170\ \text{im/s}$$

This drift velocity is substantial if the fluid flow velocity is ~1 mm/s perpendicular to the substrate, leading to a high capture probability. Furthermore, at sufficient field amplitudes magnetic nanoparticles (nanotags) may form chains along the applied field direction, which is along the short axis of the slits in FIG. 2. If the chain length is equivalent to or greater than the slit width, the nanotags will not be able to pass through the slits. The present invention makes use of this benefit of chain formation to allow high capture yield.

Figure 3:
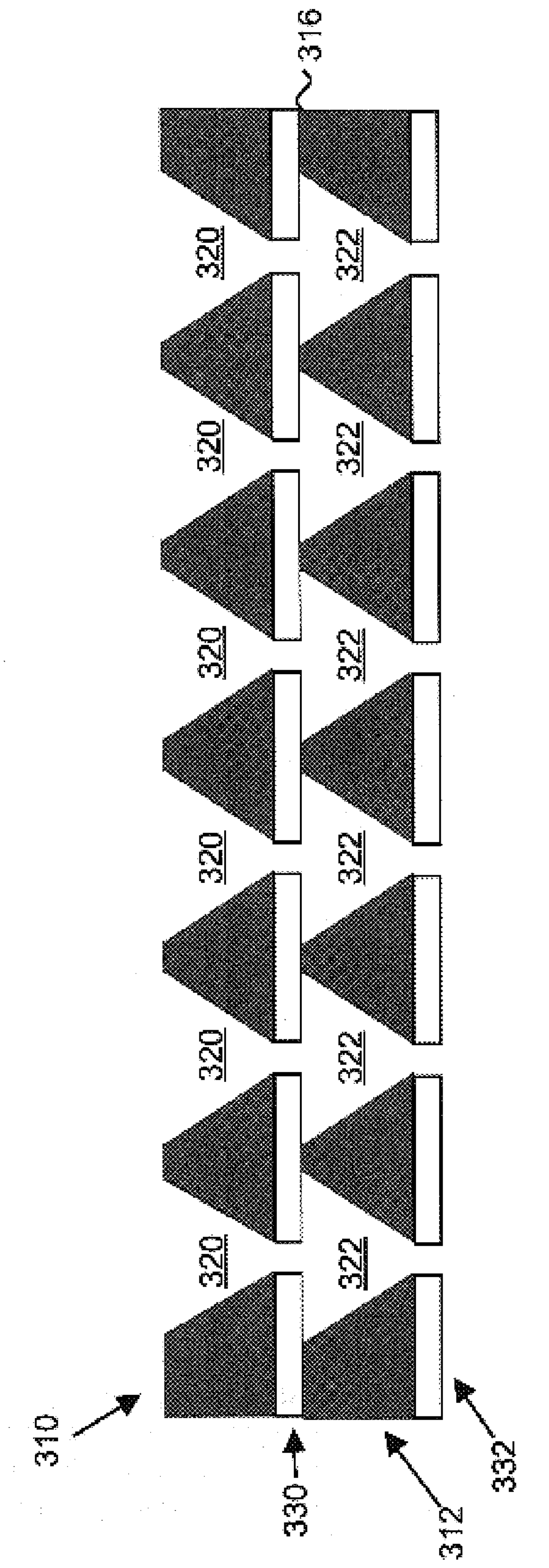
FIG. 3 shows a cross sectional view of stacked magnetic sifters according to the present invention.

The same sample can be recycled through the sifter several times to improve the capture yield if needed. Alternatively, multiple but identical substrates can be stacked in series to achieve nearly 100% capture yield ratio. For example, presume that the number of flow recycles (or the number of stacked substrates) is 3, the capture ratio in one cycle (or through one substrate in the case of stacked substrates) is 70%, then the overall capture ratio is 70%+(1-70%) 70%+(1-70%) (1-70%) 70%=97.3%. An example of stacked substrates is shown in FIG. 3. FIG. 3 shows a first substrate 310, with a first plurality of slits 320 and a first plurality of magnets 330. Magnets 330 are stacked on top surface 316 of second substrate 312, with second plurality of slits 322 and second plurality of magnets 332. Magnets 330 may be stacked directly on top surface 316, as shown, or a spacer may be used.

Figure 4:
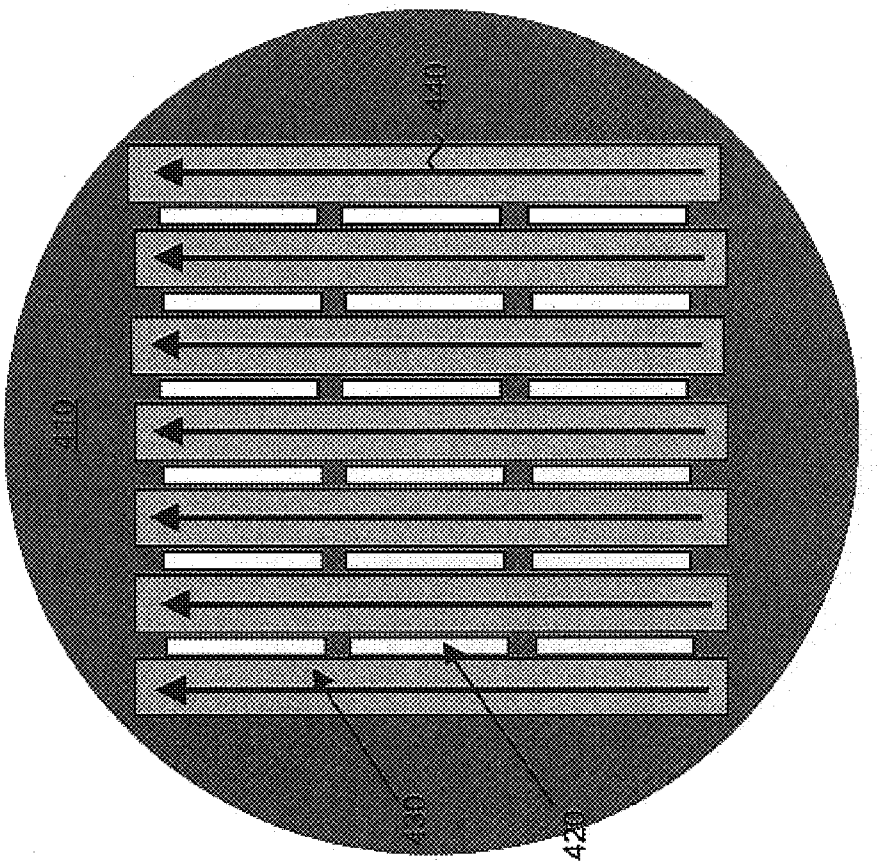
FIG. 4 shows rotation of magnetization of the magnetic sifter according to the present invention.

After the impurities are fully washed away, the trapped targets (attached to the capture probes) can be either harvested by denaturing the DNA duplex or antibody/peptide complex or kept with the nanotags without denaturing. In either case, the capture probes conjugated to the nanotags can be released from the magnetic sifter by rotating the applied field by 90°, as shown in FIG. 4, while flushing with a washing buffer. FIG. 4 shows substrate 410, slits 420, and magnets 430. The direction of the applied magnetic field is shown by bold arrows 440. The applied magnetic field is then reduced (or even removed) to prevent possible chain formation of magnetic nanotags. The magnetization will be stable along the long axis of the soft magnets because of shape anisotropy and deposited uniaxial anisotropy along the long axis of soft magnets. The magnetic field between the magnets is greatly reduced when they are magnetized in parallel, so that the nanotags can be dislodged from the edges of the magnets. If the denaturing step is skipped, then a mixture of nanotags conjugated to target molecules and nanotags with capture probes only are released from the sifter (because excess capture probes are used in FIG. 1). This mixture could be directly applied to a magnetic biochip for detection according to one scheme of the present invention, to be discussed later.

Figure 5:
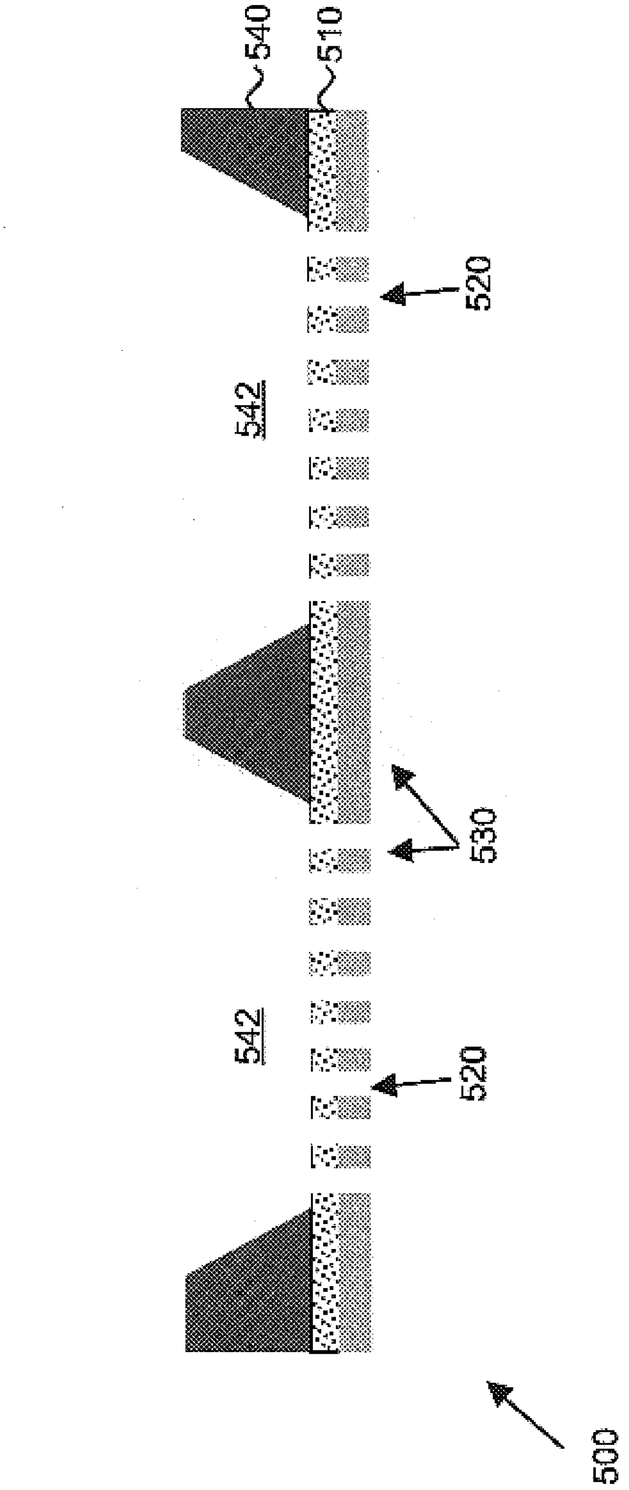
FIG. 5 shows another example of a magnetic sifter according to the present invention.

In one aspect of the present invention, shown in FIG. 5, the substrate is a thin membrane. FIG. 5 shows magnetic sifter 500, having thin substrate 510, slits 520, and magnets 530. Magnetic sifter 500 also includes a support layer 540, with a plurality of openings 542 that extend through support layer 540. Preferably, each opening 542 connects to a plurality of slits 520, as shown. Support layer 540 may be any material but is preferably silicon, e.g. (100) silicon. Thin substrate 510 may also be made of any material, but is preferably made of silicon nitride or silicon oxide. Openings 542 are preferably between about 100 μm and about 500 μm in width. Openings 542 may be tapered, as shown, but need not be.

Figure 6:
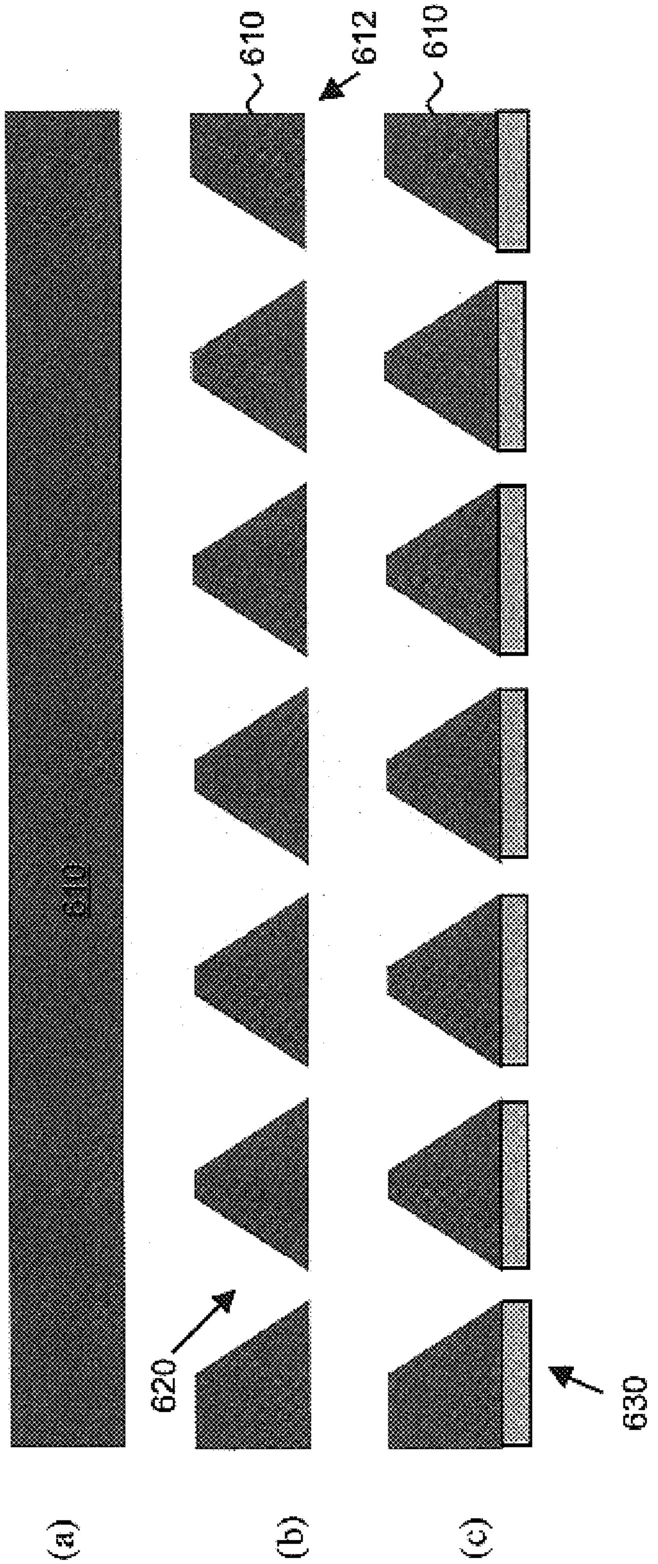
FIG. 6-8 show methods of fabricating a magnetic sifter according to the present invention.

Magnetic sifters according to the present invention may be fabricated by a number of different methods. A first method is a self-aligned fabrication method. First, a (100) Si substrate 610 is acquired and polished to an appropriate thickness, as shown in FIG. 6*a*. Then the substrate 610 is masked and anisotropically etched as shown in FIG. 6*b*, e.g., by wet etching in an alkaline solution, to create slits 620. If the aperture of the Si wafer is exposed to anisotropic etchants such as alkaline hydroxides, the (100) crystal planes (parallel to the substrate) etch much faster than the (111) crystal planes, resulting in a cavity whose side wall is parallel to the (111) planes, which will be at an angle of 54.7° with the substrate plane. Third, the bottom side 612 of the substrate 610 is coated with a layer of soft magnetic material 630 (such as NiFe, CoTaZr, CoFe alloy, CoFeHfO, or a combination of any of these materials) without a masking layer (FIG. 6*c*). In this step, the soft magnets are self aligned to the etched slits. The soft magnetic layer can also be electroplated as practiced in the magnetic recording industry after adding a conductive seed layer. Finally, the soft magnetic layer is patterned into the stripes shown in FIGS. 2 and 4. Note that the gaps of the soft magnets will have a slope, due to the non-ideal nature of film deposition processes, rather than be exactly vertical as shown in FIG. 6, but the slope can be controlled and will not hamper the operation of the magnetic sifter. In addition, the soft magnets are properly passivated to withstand the washing buffer, hybridization (or affinity binding), and denaturing solutions necessary for the biochemical procedures set forth in FIG. 1.

Figure 7:
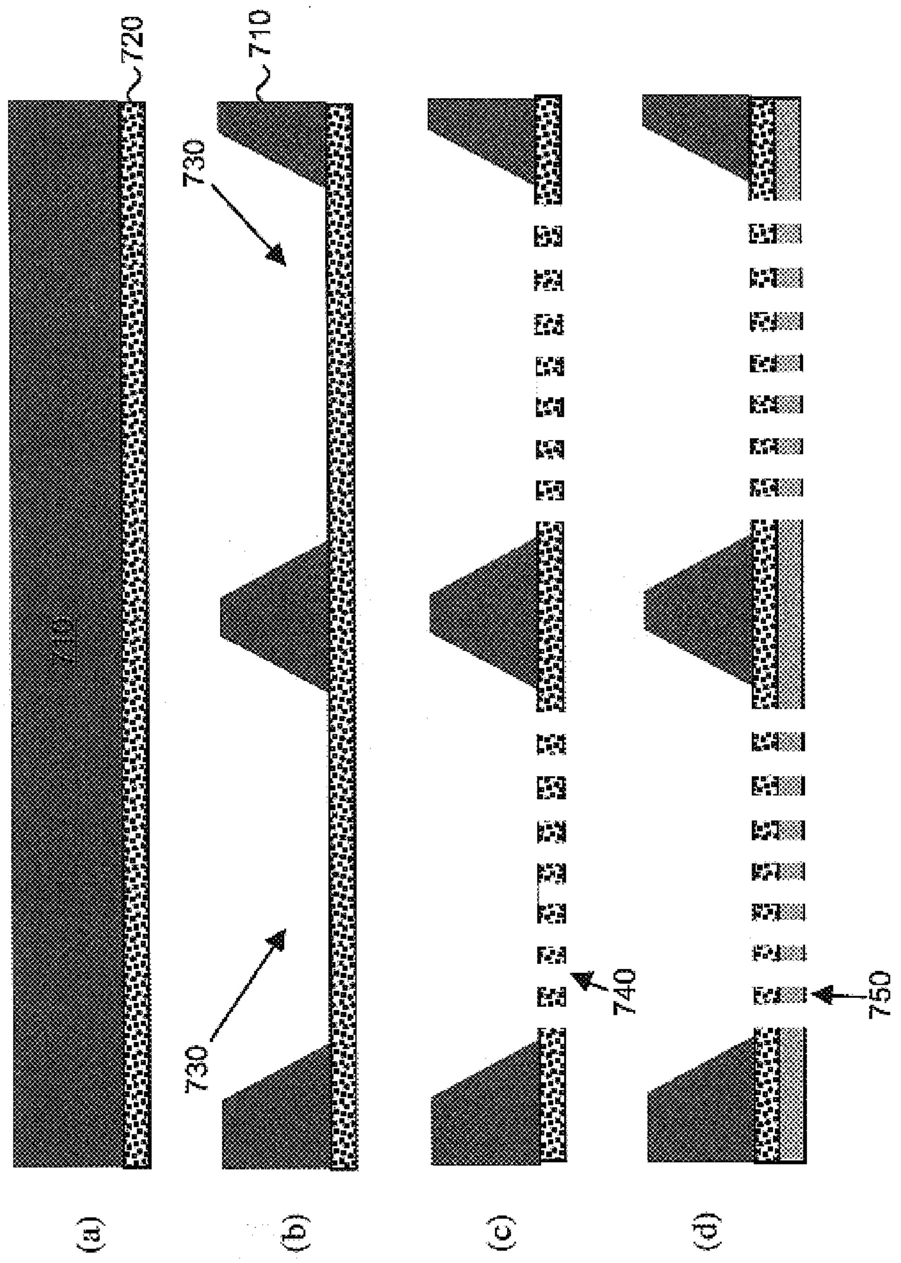

For the magnetic sifter shown in FIG. 6, the sample flow rate will be limited by the width of the slits at the bottom of the substrate or the gaps of the soft magnets, whichever is smaller. Thus, this invention also provides a self-aligned fabrication method of a micromachined magnetic sifter with a high density of slits so that the sample flow rates can be greatly enhanced compared to the magnetic sifter shown in FIG. 6. First, the bottom side of a (100) Si substrate 710 is thermally oxidized or coated with $SiN_x$ or other appropriate materials to form a membrane layer 720 (FIG. 7*a*). Then the Si substrate 710 (but not the $SiO_2$ or $SiN_x$ membrane layer) is anisotropically wet etched (FIG. 7*b*) to form openings 730. In this case the Si opening widths are much greater than those in FIG. 6. Third, the membrane layer 720 is etched (e.g., using reactive ion etching or RIE) into small rectangular slits, which are closely spaced while maintaining the mechanical strength of the membrane (FIG. 7*c*). Fourth, a soft magnetic layer is coated on the bottom side of the wafer without using a masking layer (FIG. 7*d*). Finally, the soft magnetic layer is etched into rectangular strips similar to those shown in FIG. 2 except that their widths and gaps are much smaller. The dimensions of the strips are limited only by the thickness of the membrane layer and the RIE process.

The sample flow rate is limited by the width of the membrane slits. Since the membrane slits in the sifter shown in FIG. 7 can effectively occupy a much greater fraction of the Si substrate than in the sifter shown in FIG. 6, a much higher flow rate is achieved. Furthermore, the smaller gaps between the soft magnets lead to a higher field gradient, which is desirable for a higher capture ratio.

Figure 8:
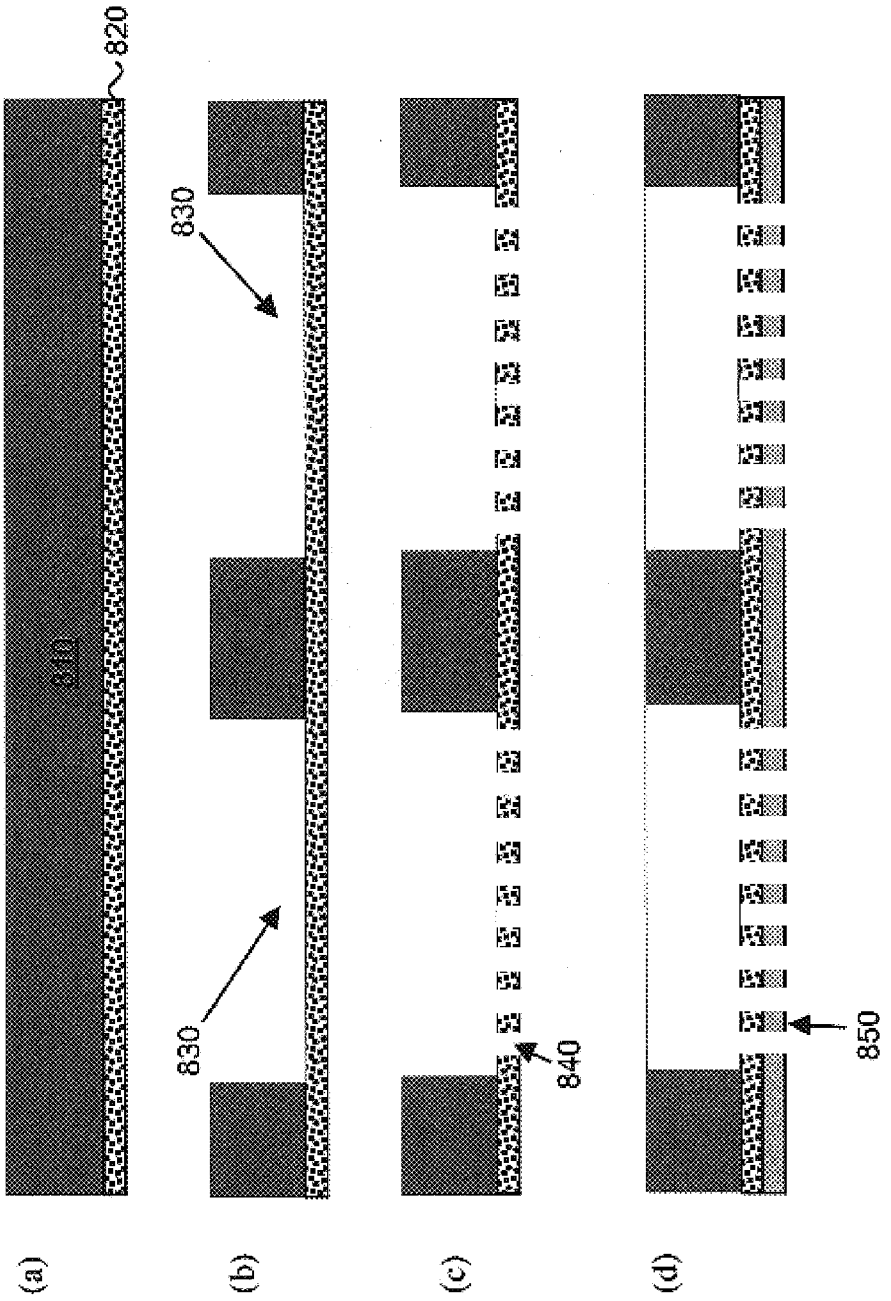

A third fabrication process is shown in FIG. 8. With this method, approximately 1 μm of $SiN_x$ (low stress) is deposited on an about 375 μm thick double polished Si (100) wafer 810 to form a thin membrane 820 (FIG. 8*a*). Next, a first mask is used to anisotropically dry etch the Si to give openings 830 with side walls of nearly 90° (FIG. 8*b*). Third, the SiNx layer 820 is anisotropically dry etched using a second mask to give slits 840 (FIG. 8*c*). Photoresist can then be coated around the active region with a third mask. Next, approximately 1 μm of NiFe 850 is sputter plated (or electroplated, if needed) (FIG. 8*d*). Unwanted NiFe is then lifted off and the NiFe is passivated if needed. Finally, the wafers may be diced and bonded to syringes.

A key issue in the fabrication process shown in FIG. 8 is that the width of the etched cavities at the bottom may vary. If the thickness varies by ±15 μm, and the dry etch sidewall angle is 10 degrees, then the bottom width may be 66±3 μm narrower than the top width. The design of the second mask must tolerate this variation. Thus, the Si bottom openings are designed to be 200 μm wide, and each side may vary by ±3 μm, so the $SiN_x$ slits are chosen to be approximately 11 μm away. Each 200 μm width bottom translates into 200 μm+2×66 μm=332 μm. If the length of the cavities is also chosen to be 332 μm, one can fit about $\pi\times(2.5\text{ mm})^2/(0.332\text{ mm})^2=\sim178$ in one syringe. If 25% of 200 μm×200 μm $SiN_x$ is etched, and the flow speed at the bottom of the slits is 1 mm/s, then the flow rate is $25\%\times178\times0.04\text{ mm}^2\times1\text{ mm/s}=1.8$ μl/s or 0.11 ml/min. This allows capture of a large number of capture probes.

Figure 9:
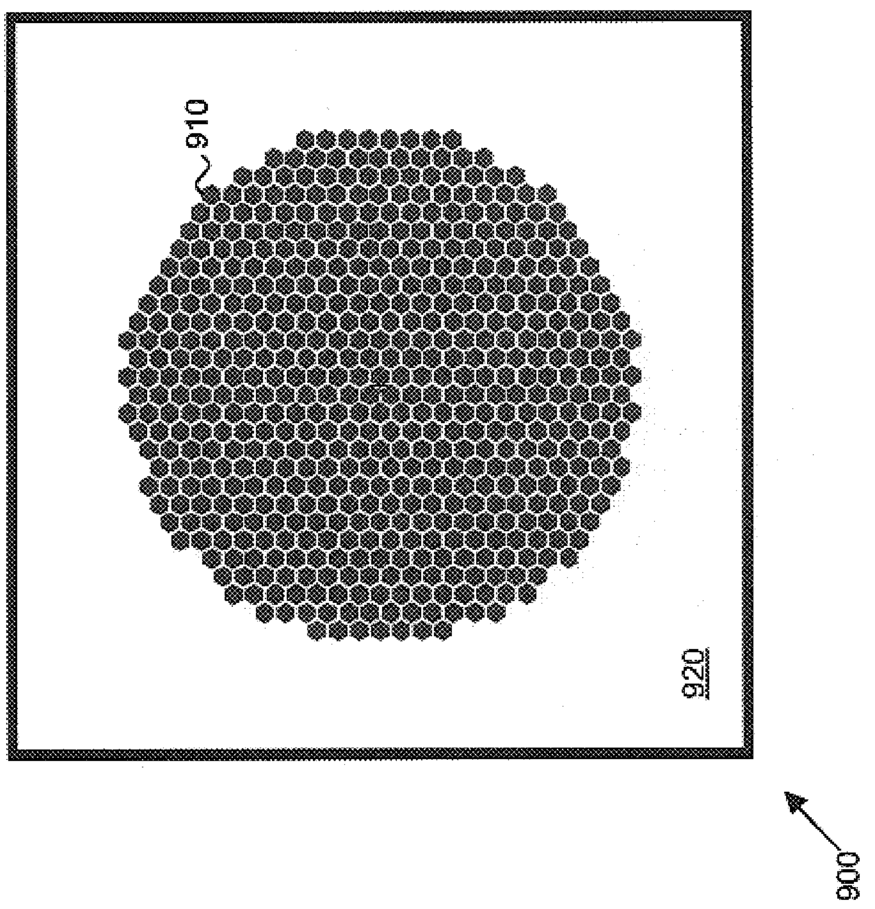
FIG. 9 shows a bottom view of a magnetic sifter in a honeycomb configuration according to the present invention.
Figure 10:
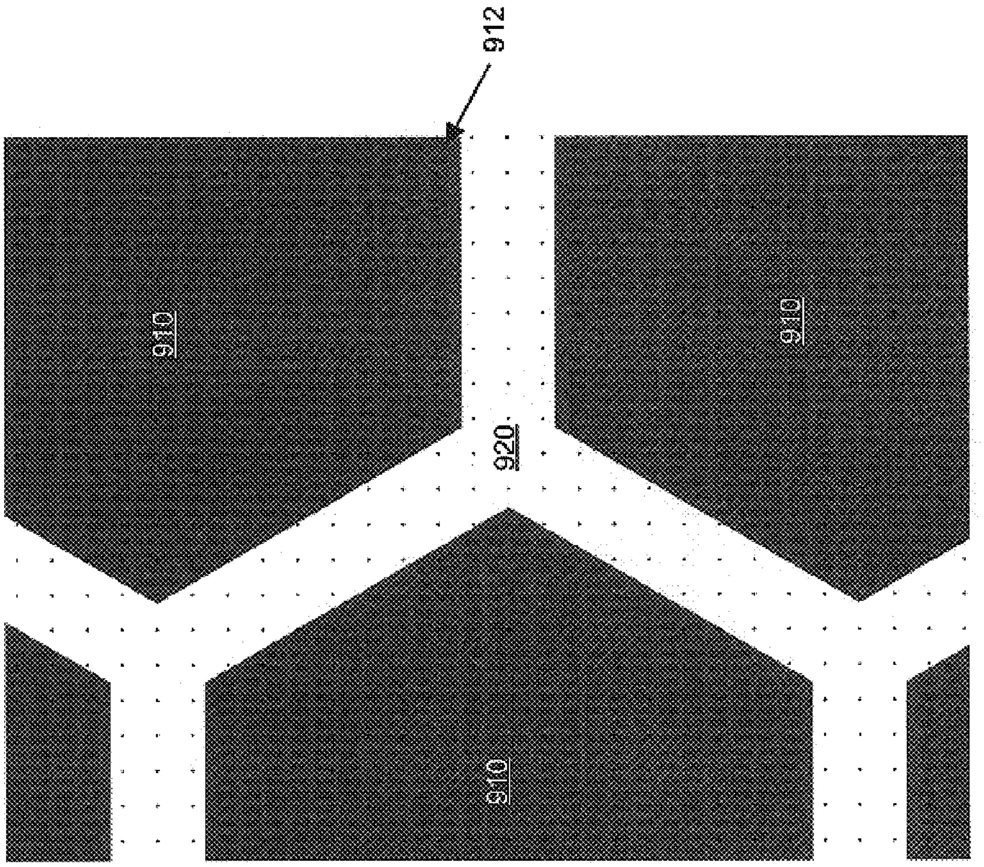
FIG. 10 shows a detailed plan of the magnetic sifter shown in FIG. 9.
Figure 11:
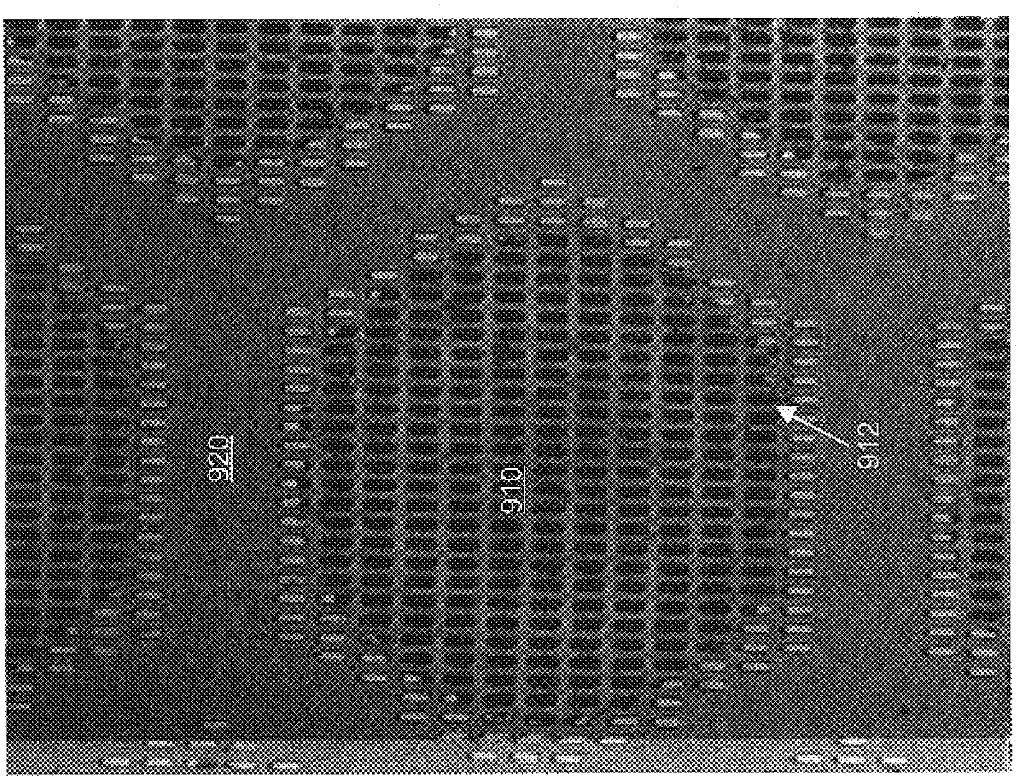
FIG. 11 shows a micrograph of a magnetic sifter fabricated according to FIG. 9-10.

FIG. 9 shows a preferred layout for a magnetic sifter 900 according to the present invention. The size of the slits in each honeycomb 910 is preferably around 2 μm×5 μm. The white areas surrounding and between honeycombs is unetched Si/SiNx 920, which provides rigidity to the sifter. A diagram of the layout of individual honeycombs 910, with slits 912, is shown in FIG. 10. The grid step size is 10 μm in this layout, and is preferably in the range of about 5 to 20 μm. FIG. 11 shows a micrograph of a fabricated magnetic sifter according to the present invention, with unetched Si/SiNx 920, honeycombs 910, and slits 912 indicated.

Figure 12:
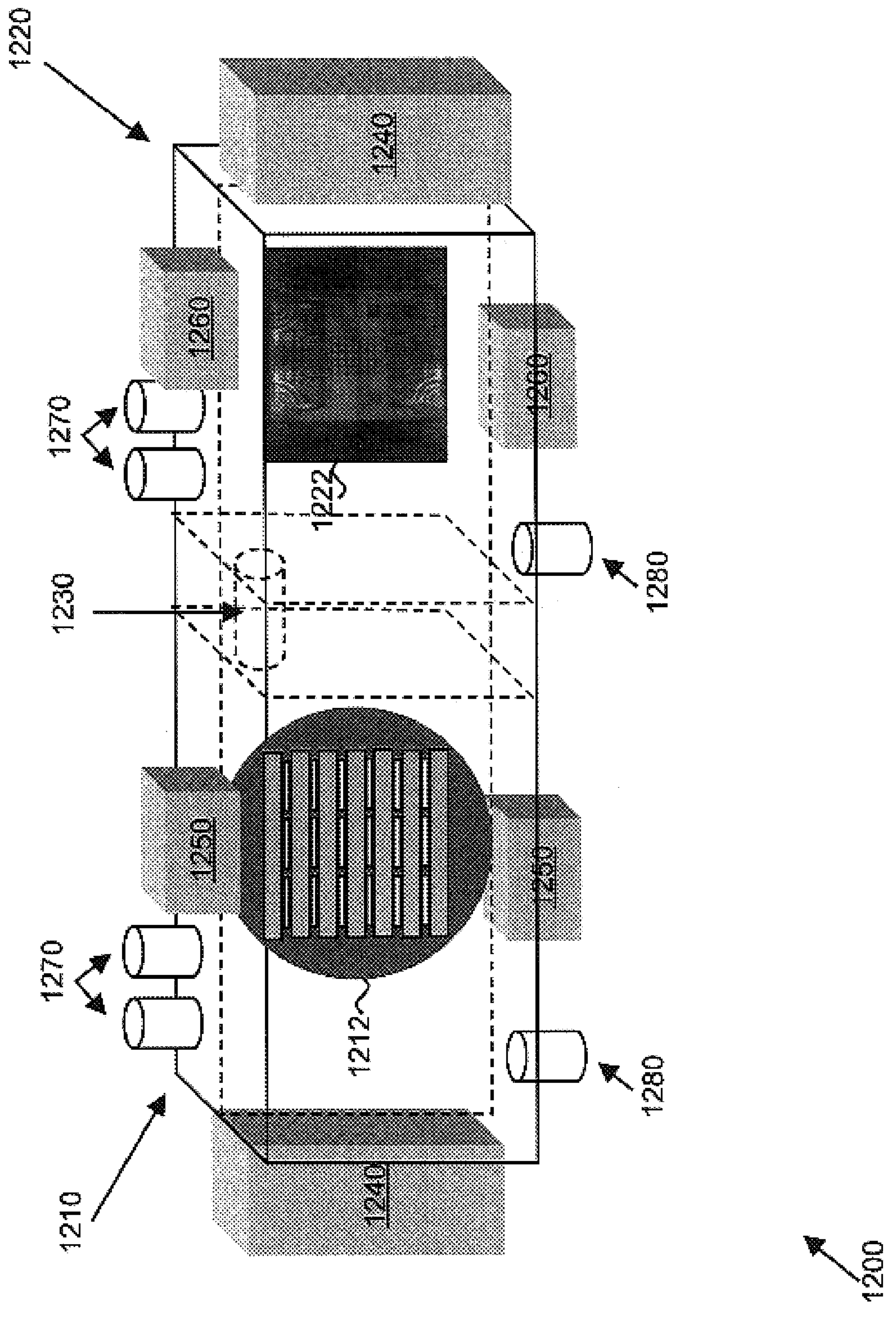
FIG. 12 shows an example of a magnetic sifter in fluidic connection with a detection chamber according to the present invention.

A key element of the present invention is that the released nanotags and capture probes can be optionally reused as detection probes to "stain" the same target molecules which are eventually immobilized on a magnetic biochip (see U.S. patent application Ser. No. 10/829505, filed Apr. 22, 2004 for details on using nanotags as detection probes). At that stage the nanotags generate a magnetic signal, which can be used to identify and quantify the target molecules on the biochip. Thus, the present invention also provides an integrated magnetic biosensor with a sample preparation chamber 1210 and detection chamber 1220 in one cartridge 1200 as illustrated in FIG. 12. The two chambers are interconnected with a fluidic channel 1230. After mixing the raw sample containing target DNA/RNA fragments (or proteins) with capture probes, the mixture is delivered to the sample preparation chamber 1210 of the cartridge 1200 via one of the inlets 1270, and the impurities are washed away from one of the outlets 1280 while the targets are trapped by the magnetic sifter 1212. In one embodiment of the present invention, the nanotag-labeled targets are first released as shown in FIG. 4 and subsequently delivered to a detection chamber 1220 containing a MagArray® chip 1222 (see U.S. application Ser. No. 10/829,505, filed Apr. 22, 2004, which is incorporated by reference herein). The nucleic acid or protein targets are then interrogated. The inlets, 1270, outlets 1280 and interconnect fluidic channel 1230 are all equipped with valves (not shown). The compact cartridge 1200 is situated near three pairs of electromagnets: 1240 is for applying the longitudinal bias field (relatively small) to the magnetic sifter 1212 (when releasing the nanotags) and to the magnetic sensors on the MagArray® chip 1222; 1250 is for saturating the soft magnets when trapping the nanotags; 1260 is for applying modulation field to the MagArray® chip 1222 during the magnetic readout of nanotags bound on the MagArray® chip 1222.

In another embodiment of the present invention, after washing away the impurities the captured targets in the sample preparation chamber 1210 are harvested with a denaturing step before releasing the nanotags. These targets are subsequently delivered to detection chamber 1220 to bind with immobilized probes on the MagArray® chip 1222. Then the nanotag-labeled probes are released from the sample preparation chamber and delivered to the detection chamber 1220 to "stain" the specific targets bound on the chip. To speed up the staining process, one can optionally inject additional nanotag-labeled probes to the detection chamber 1220 in this step. Afterwards the MagArray® chip 1222 is read out to identify and quantify the targets present in the original sample.

The magnetic sifter in combination with magnetically tagged target molecules has many applications in the biological sciences. For example, DNA, RNA, proteins, and pathogens may be detected. In addition, targets that are part of a cell or organism may be identified. Finally, target molecules may be biomarkers of disease, including, but not limited to, cancer, heart disease, neurological disease and infectious disease. The examples of such applications provided below are for illustrative purposes only, and do not limit the scope of the present invention.

The nanotag-labeled probes shown in FIG. 1 can be used for pathogen extraction as well as pathogen detection. For example, important pathogens in sepsis include *candida, staphylococcus, enterobacterium*, and *E. coli*, among others. These pathogen targets can be fished out of a raw sample using the magnetic sifter with capture probes that hybridize with an oligomer of each target. The denatured pathogen targets can then be hybridized to a magnetic biochip. The immobilized probes at each site hybridize to another oligomer of each pathogen target. Afterwards the released nanotag-labeled capture probes can be used as detection probes to "stain" the magnetic biochip. Finally, the identity and quantity of each pathogen target can be read out magnetically by counting the number of nanotags at each specific site of the chip.

The above scheme can be adapted for human papillomavirus (HPV) detection and genotyping. For example, the capture probes can be oligomers that bind to the common ends of the E1 region of numerous HPV types. After releasing the various E1 regions from the magnetic sifter, their polymorphisms can be interrogated by a magnetic biochip in a similar manner. Of course, the immobilized probes in this case are specific probes complementary to the E1 regions of targeted HPV types.

Nanotag-labeled probes can also be used for human genomic DNA sample extraction and profiling. In short tandem repeat (STR) based DNA profiling and human identification using, e.g., the Combined DNA Index System (CODIS), a unique set of 13 loci in non-coding regions of human DNA are used to identify any person based on the STR alleles at each locus. Each locus is flanked by specific oligomers. Therefore, 13 capture probes can be designed that are complementary to the flanking oligomers of all 13 loci. The capture probes can then be labeled with magnetic nanotags. Using the magnetic sifter shown in FIG. 1 these probes can separate all the STR-containing DNA fragments out of a raw sample after lysis. The STR alleles can then be interrogated with microarrays with variable length probes either by enzymatic digestion, as described in U.S. patent application Ser. No. 11/125,558, filed May 10, 2005, or by branch migration assay, as described in U.S. patent application Ser. No. 11/231,657, filed Sep. 20, 2005, both of which are incorporated by reference herein. For example, as, nanotag-labeled capture probes hybridized with three-repeat STR targets may be further hybridized with variable length probes, ranging from one to three repeats, on a magnetic microarray. After enzymatic digestion with a single strand nuclease, or branch migration assay, the nanotags at the sites having variable length probes with one or two STR repeats will be removed while those at the site with three repeats remain. The step change in the signal strength from the first two sites to the third site will indicate the presence of the three-repeat STR allele. By spotting all the probes covering all the alleles of the 13 loci specified by CODIS in a single magnetic microarray, one can uniquely identify any person with magnetic nanotag-labeled capture/detection probes.

Nanotag-labeled probes can also be used for protein extraction and profiling such as in proteomics-based biomarker validation and cancer diagnostics. Nanotag-tethered antibody probes can capture specific protein targets. Then the protein targets can be delivered to a magnetic microarray with immobilized probes (such as aptamers or antibody probes) which specifically bind the protein targets that have already been labeled with magnetic nanotags. The protein targets can eventually be identified and quantified by magnetically detecting the nanotags at various sites on the microarray.

While it is advantageous to use the same probes for both capture and detection of target molecules as set forth, it is possible and sometimes preferable to use slightly or entirely different probes and labels in the capture and detection of target molecules. While magnetic labels must be used in conjunction with the magnetic sifter, other labels such as fluorescent dyes can be used in the detection of target molecules.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A magnetic sifter, comprising:

a) at least one substrate, wherein each of said at least one substrates contains a plurality of slits, and wherein each slit extends through said at least one substrate;

b) a plurality of magnets attached to a bottom surface of said substrate, wherein said plurality of magnets are proximal to openings of said plurality of slits; and c) an electromagnetic source, wherein said source controls the magnitude and direction of a magnetic field gradient generated by said plurality of magnets.

2. The magnetic sifter as set forth in claim 1, wherein said magnets comprise a soft magnetic material.

3. The magnetic sifter as set forth in claim 1, wherein each of said at least one substrates comprises silicon.

4. The magnetic sifter as set forth in claim 1, wherein each of said at least one substrates comprises a thin membrane.

5. The magnetic sifter as set forth in claim 4, wherein said thin membrane comprises silicon nitride.

6. The magnetic sifter as set forth in claim 4, wherein each of said at least one substrates further comprises a support layer, wherein said support layer comprises a plurality of openings, and wherein each of said openings extends through said support layer.

7. The magnetic sifter as set forth in claim 6, wherein said support layer comprises silicon.

8. The magnetic sifter as set forth in claim 6, wherein said openings in said support layer are between about 100 μm and about 500 μm in width.

9. The magnetic sifter as set forth in claim 6, wherein each of said openings in said support layer connects to a plurality of said slits in said substrate.

10. The magnetic sifter as set forth in claim 1, wherein each of said plurality of slits is rectangular in shape.

11. The magnetic sifter as set forth in claim 1, wherein the width of each of said plurality of slits at said bottom surface of said substrate is between about 0.5 μm and about 10 μm.

12. The magnetic sifter as set forth in claim 1, wherein said electromagnetic source generates a magnetic field gradient at said openings of said slits in the range of about 0.01 T/μm to about 1 T/μm.

13. The magnetic sifter as set forth in claim 1, comprising at least a first substrate, a first plurality of slits, and a first plurality of magnets, and a second substrate, with a second plurality of slits and a second plurality of magnets, wherein said first plurality of magnets is stacked onto a top surface of said second substrate.

14. The magnetic sifter as set forth in claim 1, wherein the distance between neighboring slits is between about 0.5 μm and about 10 μm.

15. The magnetic sifter as set forth in claim 1, comprising at least two electromagnetic sources, wherein said two electromagnetic sources are separated by 90 degrees.

16. The magnetic sifter as set forth in claim 1, further comprising a detection chamber in fluidic connection with said magnetic sifter.

17. A method of preparing a biological sample with the magnetic sifter as set forth in claim 1, comprising:

a) mixing said biological sample with capture probes, wherein said capture probes are labeled with magnetic tags, and wherein said capture probes bind at least one target biomolecule in said biological sample;

b) generating a magnetic field gradient in said magnetic sifter with said electromagnetic source; and c) passing said mixture through said magnetized magnetic sifter, wherein said magnetic sifter captures said capture probes bound to said at least one target biomolecule.

18. The method as set forth in claim 17, further comprising:

d) releasing said capture probes bound to said at least one target biomolecule from said magnetic sifter, wherein said releasing comprises rotating the direction of applied electromagnetic field by 90 degrees to reduce the magnitude of said magnetic field gradient and flushing said magnetic sifter with a washing buffer.

19. The method as set forth in claim 17, wherein said capture probe comprises at least one of a nucleic acid with a sequence that is complementary to said target biomolecule or an antibody that binds to said target biomolecule.

20. The method as set forth in claim 17, further comprising harvesting said target biomolecule.

21. The method as set forth in claim 20, wherein said target molecule is a biomarker of a disease.

22. The method as set forth in claim 21, wherein said disease is at least one of cancer, heart disease, neurological disease or infectious disease.

23. The method as set forth in claim 17, further comprising detecting the presence of said target biomolecule.

24. The method as set forth in claim 17, wherein said target biomolecule is at least one of DNA, RNA, protein, or pathogen.

25. The method as set forth in claim 17, wherein said target biomolecule is part of a cell or organism.

26. The method as set forth in claim 25, wherein said organism is *candida, staphylococcus, enterobacterium, E. Coli*, and human papillomavirus.

27. The method as set forth in claim 17, wherein said magnetic tags comprise nanotags or magnetic beads.

* * * * *